United States Patent
Morishita

(10) Patent No.: US 11,377,632 B2
(45) Date of Patent: Jul. 5, 2022

(54) PRODUCTION METHOD FOR BACTERIAL CELLS

(71) Applicant: IDEMITSU KOSAN CO., LTD., Chiyoda-ku (JP)

(72) Inventor: Yasuyuki Morishita, Chiyoda-ku (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 100 days.

(21) Appl. No.: 16/650,199

(22) PCT Filed: Sep. 25, 2018

(86) PCT No.: PCT/JP2018/035361
§ 371 (c)(1),
(2) Date: Mar. 24, 2020

(87) PCT Pub. No.: WO2019/059396
PCT Pub. Date: Mar. 28, 2019

(65) Prior Publication Data
US 2020/0277564 A1 Sep. 3, 2020

(30) Foreign Application Priority Data
Sep. 25, 2017 (JP) .............................. JP2017-183587

(51) Int. Cl.
*C12N 1/20* (2006.01)
(52) U.S. Cl.
CPC ...................... *C12N 1/20* (2013.01)
(58) Field of Classification Search
None
See application file for complete search history.

(56) References Cited

U.S. PATENT DOCUMENTS

| 2016/0237512 A1 | 8/2016 | Inai et al. |
| 2019/0048311 A1 | 2/2019 | Eguchi et al. |
| 2020/0040300 A1 | 2/2020 | Morishita |
| 2020/0277564 A1* | 9/2020 | Morishita ................ C12N 1/20 |

FOREIGN PATENT DOCUMENTS

| CN | 105296409 A | 2/2016 | |
| GB | 1298668 A | * 12/1972 | ............. C12N 15/01 |
| RU | 2 213 780 C2 | 10/2003 | |

(Continued)

OTHER PUBLICATIONS

Extended European Search Report dated May 10, 2021 in European Patent Application No. 18858962.6, 10 pages.

(Continued)

*Primary Examiner* — Richard C Ekstrom
(74) *Attorney, Agent, or Firm* — Oblon, McClelland, Maier & Neustadt, L.L.P.

(57) ABSTRACT

The present invention provides a method for producing bacterial cells, which comprises, in a multi-stage liquid culture process for bacteria, culturing a bacterium in a liquid medium containing an antibiotic in a stage prior to the final stage, and then lowering the concentration of the antibiotic in the final stage to a level lower than that in the prior stage. Accordingly, bacterial cells can be produced with good productivity while suppressing the appearance of variants forming abnormal colonies among the bacteria obtained after culture.

3 Claims, 1 Drawing Sheet

(56) References Cited

FOREIGN PATENT DOCUMENTS

| WO | WO 2015/056666 A1 | 4/2015 |
|----|---|---|
| WO | WO 2016/163534 A1 | 10/2016 |
| WO | WO 2018/066686 A1 | 4/2018 |

OTHER PUBLICATIONS

Lee. J., et al., Enhanced Production of α-Amylase in Fed-Batch of *Bacillus subtilis* TN106[pAT5], Biotechnology and Bioengineering, vol. 42, No. 1, 1993, XP55799460, pp. 1142-1150.
International Search Report dated Jan. 8, 2019 in PCT/JP2018/035361, 2 pages.
K. Ochi et al., "Effect of Antibiotics on Sporulation Caused by the Stringent Response in *Bacillus subtilis*", Journal of General Microbiology, 1983, vol. 129, pp. 3709-3720.
G. E. Carlisle et al., "Enzyme Activities and Antibiotic Susceptibility of Colonial Variants of *Bacillus subtilis* and *Bacillus licheniformis*", Applied and Environmental Microbiology, 1989, vol. 55, No. 11, pp. 3026-3028.
S. M. Monteiro et al., "A Procedure for High-Yield Spore Production by *Bacillus subtilis*", Biotechnology Progress, 2005, vol. 21, No. 4, 1026-1031 and cover page.
C. Luo et al., "*Bacillomycin* L and surfactin contribute synergistically to the phenotypic features of *Bacillus subtilis* 916 and the biocontrol of rice sheath blight induced by *Rhizoctonia solani*", Appl Microbiol Biotechnol, 2015, vol. 99, No. 4, pp. 1897-1910.
Z-r. Gu et al., "Improvement of antifungal activity of *Bacillus subtilis* G3 by mutagenesis with acri-dine orange", Acta Phytopathologica Sinica, 2008, vol. 38, No. 2, pp. 185-191 with its English abstract.
M. Berditsch et al., "The Ability of *Aneurinibacillus migulanus* (*Bacillus brevis*) to Produce the Antibiotic Gramicidin S is Correlated with Phenotype Variation", Applied and Environmental Microbiology, 2007, vol. 73, No. 20, pp. 6620-6628.

\* cited by examiner

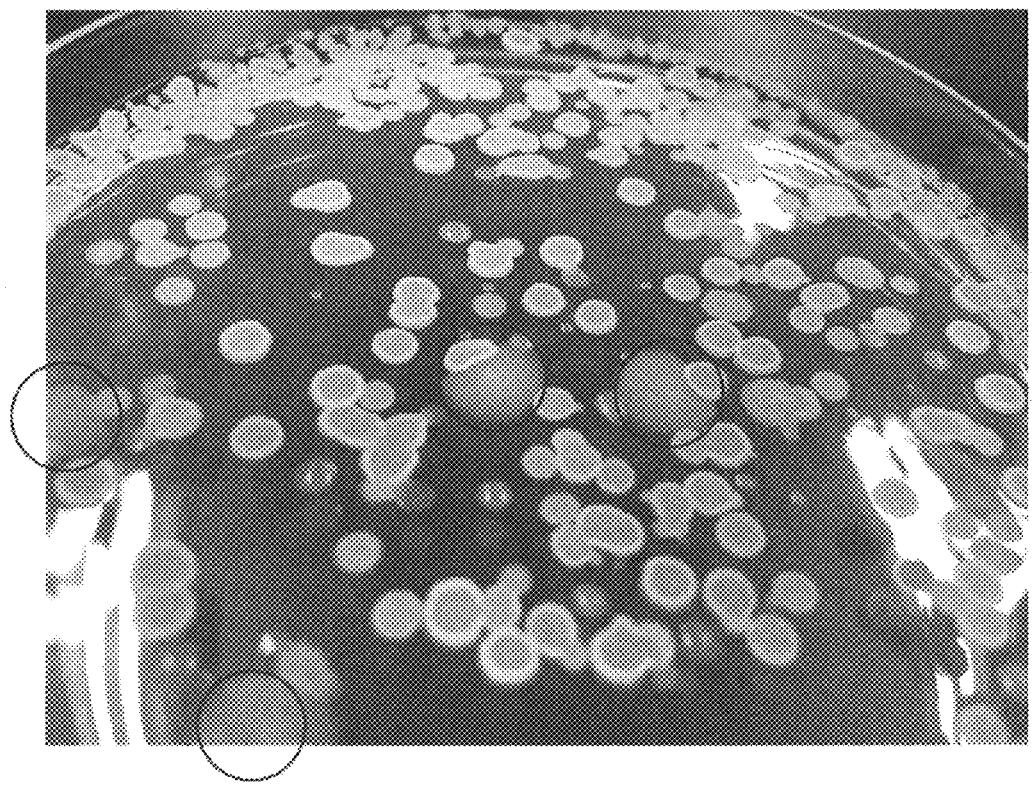

PRODUCTION METHOD FOR BACTERIAL CELLS

TECHNICAL FIELD

The present invention relates to a method for producing bacterial cells with good productivity while suppressing the occurrence and the growth of variants forming abnormal colonies, which can occur during multi-stage liquid culture of bacteria.

BACKGROUND ART

Bacteria are used in various fields such as production of enzymes and useful substances, production of fermented foods, decomposition of organic matter, medicines for intestinal disorders, microbial pesticides, and microbial fertilizers.

In any field, culturing bacteria is required for preparation of bacterial cells. However, there are cases where variants exhibiting abnormalities in colony morphology appear during culture and grow predominantly over the cells having the original properties, and thus the cells have lost the original useful properties after the completion of culture.

For example, Non-Patent Literature 1 describes an observed phenomenon in which variants exhibiting abnormalities in colony morphology etc., appear during the passage of several thousand generations of a *Bacillus* bacterium in liquid medium, and grow in preference to the original cells, thereby completely replacing the original cells. It is presumed that such a phenomenon is caused by the fact that variants are specialized in a specific culture environment to eliminate an unnecessary metabolic system and grow predominantly over the original cells.

Non-Patent Literature 2 describes that a biosynthetic ability-deficient variant, which is deficient in biosynthesis of Bacillomycin L and Surfactin, of *Bacillus subtilis* 916 strain, exhibits colony morphology different from that of the wild-type strain. Bacillomycin L and Surfactin are known to exhibit controlling effects on some plant diseases. Hence, this is considered as an example in which a mutation in colony morphology and the loss of useful properties are linked.

Further, Non-Patent Literature 3 describes an example in which the production amount of Itulin A is increased in a strain having altered colony morphology compared with the parent strain in the course of breeding for enhancing the antibacterial activity of *Bacillus subtilis* G3 strain.

Non-Patent literature 4 describes that regarding *Aneurinibacillus migulanus* (old classification: *Bacillus brevis*) ATCC 9999 strain, six types of colony morphology were detected in the culture collection deposit strain and differed in Gramicidin S productivity.

Non-Patent Literature 5 describes an example in which colony morphology variant strains of *Bacillus subtilis* VT30M strain and *Bacillus licheniformis* VT3 strain exhibited enzyme productivity and antibiotic resistance differing from those of the wild-type strains.

CITATION LIST

Non-Patent Literature

[Non-Patent Literature 1] Biotechnology progress 2005, 21, 4, 1026-1031
[Non-Patent Literature 2] Appl. Microbiol. Biotechnol. 2015, 99, 4 1897-1910
[Non-Patent Literature 3] Zhiwu Bingli Xuebao 2008, 38, 2, 185-191
[Non-Patent Literature 4] Appl. Environ. Microbiol. 2007, 73, 20, 6620-6628
[Non-Patent Literature 5] Appl. Environ. Microbiol. 1989, 55, 3026-3028

SUMMARY OF INVENTION

As described above, in liquid culture, particularly multi-stage liquid culture of bacteria is problematic in that variants exhibiting abnormalities in colony morphology appear during culture, grow predominantly over the cells having original properties, and thus the original useful properties of cells may be impaired after completion of culture. Any efficient technique for suppressing such a phenomenon has not been reported to date.

Therefore, an object of the present invention is to provide a novel method for producing bacterial cells with good productivity while suppressing the appearance of variants exhibiting abnormalities in colony morphology among bacterial cells obtained after culture in a multi-stage liquid culture process for bacteria.

As a result of intensive studies to achieve the above object, the present inventor has discovered that bacterial cells can be produced with good productivity while significantly reducing the appearance of variants exhibiting abnormalities in colony morphology from among a bacterial population obtained after the completion of culture by, in a multi-stage liquid culture process, culturing a bacterium using a medium containing an antibiotic in a stage prior to the final stage and then lowering the concentration of the antibiotic in the final stage to a level lower than that in the prior stage. Hence, the present inventor has completed the present invention.

The present invention is as follows.

[1] A method for producing bacterial cells, comprising, in a multi-stage liquid culture process for bacteria, culturing a bacterium in a liquid medium containing an antibiotic in a stage prior to the final stage, and then lowering the concentration of the antibiotic in the final stage to a level lower than that in the prior stage.

[2] The method according to [1], wherein the bacterium is a spore-forming bacterium.

[3] The method according to [2], wherein the spore-forming bacterium belongs to the genus *Bacillus*.

[4] The method according to [3], wherein the spore-forming bacterium is selected from the group consisting of *Bacillus subtilis, Bacillus amyloliquefaciens, Bacillus pumilus, Bacillus simplex, Bacillus lentus, Bacillus laterosporus, Bacillus alvei, Bacillus popilliae, Bacillus licheniformis, Bacillus brevis, Bacillus stearothermophilus, Bacillus alcalophilus, Bacillus coagulans, Bacillus circulans, Bacillus siamensis, Bacillus lautus, Bacillus clausii, Bacillus megaterium, Bacillus thuringiensis, Bacillus cereus, Bacillus firmus, Bacillus velezensis, Bacillus pichinotyi, Bacillus acidocaldarius, Bacillus alkalicola, Bacillus azotoformans, Bacillus anthracis, Bacillus badius, Bacillus bataviensis, Bacillus cycloheptanicus, Bacillus aneurinilyticus, Bacillus migulanus, Bacillus abyssalis, Bacillus aestuarii, Bacillus polymyxa* and *Bacillus sp*.

[5] The method according to any one of [1] to [4], wherein the antibiotic is at least one antibiotic selected from the group consisting of streptomycin, lincomycin, erythromycin, rifampicin, chloramphenicol, actinomycin, fusidic acid, lipiamycin, puromycin, spectinomycin, tetracycline and thiostrepton.

[6] The method according to [5], Wherein the antibiotic is streptomycin.

[7] The method according to any one of [1] to [6], wherein the concentration of the antibiotic in the liquid medium in the stage prior to the final stage ranges from 0.001 ppm to 10,000 ppm.

[8] The method according to any one of [1] to [6], wherein the concentration of the antibiotic in the liquid medium in the stage prior to the final stage ranges from 1.0 ppm to 90 ppm.

[9] A method for culturing a bacterium exhibiting the reduced appearance of variants forming an abnormal colony, comprising, in a multi-stage liquid culture process for bacteria, culturing a bacterium in a liquid medium containing an antibiotic in a stage prior to the final stage, and then lowering the concentration of the antibiotic in the final stage to a level lower than that in the prior stage.

[10] A method for suppressing an appearance and a growth of variants forming an abnormal colony during liquid culture of bacteria, comprising, in a multi-stage liquid culture process for bacteria, culturing a bacterium in a liquid medium containing an antibiotic in a stage prior to the final stage, and then lowering the concentration of the antibiotic in the final stage to a level lower than that in the prior stage.

Effects of Invention

According to the present invention, an antibiotic is contained in a medium to be used for multi-stage culture for culturing bacteria, and then the amount of the antibiotic in the final stage is reduced, so that bacterial cells can be produced with good productivity while reducing the proportion of variants exhibiting abnormalities in colony morphology at the time of completion of liquid culture of bacteria. Variants exhibiting abnormalities in colony morphology are likely to have lost desirable properties. Hence, through reduction of such variants, the thus cultured and obtained bacterial cells can be used in a preferable state for applications such as production of enzymes and useful substances, production of fermented foods, decomposition of organic matter, medicines for intestinal disorders, microbial pesticides and microbial fertilizers.

BRIEF DESCRIPTION OF DRAWING

The drawing is a photograph showing an example of the forms of abnormal colonies. Abnormal colonies are indicated with ○.

DESCRIPTION OF EMBODIMENTS

In the present invention, the kinds of a bacterium are not particularly limited. As long as the bacterium can be cultured by liquid culture and are capable of forming colonies on solid medium, the bacterium may be gram-positive or gram-negative. Examples thereof include bacteria of the genus *Escherichia*, bacteria of the genus *Shigella*, bacteria of the genus *Salmonella*, bacteria of the genus *Klebsiella*, bacteria of the genus *Yersinia*, bacteria of the genus *Enterobacter*, bacteria of the genus *Pseudomonas*, bacteria of the genus *Brucella*, bacteria of the genus *Staphylococcus*, bacteria of the genus *Streptococcus*, bacteria of the genus *Streptomyces*, bacteria of the genus *Rhodococcus*, bacteria of the genus *Acetobacterium*, bacteria of the genus *Methanobacterium*, bacteria of the genus *Enterococcus*, bacteria of the genus *Bacillus*, bacteria of the genus *Clostridium*, bacteria of the genus *Corynebacterium*, and bacteria of the genus *Mycobacterium*.

Of these bacteria, spore-forming bacteria such as those belonging to the genus *Bacillus*, the genus *Paenibacillus*, the genus *Geobacillus*, the genus *Clostridium*, or the genus *Sporosarcina* are more preferable.

Examples of bacteria of the genus *Bacillus* are not particularly limited as long as they are classified under the genus *Bacillus*, and include *Bacillus subtilis*, *Bacillus amyloliquefaciens*, *Bacillus pumilus*, *Bacillus simplex*, *Bacillus lentus*, *Bacillus laterosporus*, *Bacillus alvei*, *Bacillus popilliae*, *Bacillus licheniformis*, *Bacillus brevis*, *Bacillus stearothermophilus*, *Bacillus alcalophilus*, *Bacillus coagulans*, *Bacillus circulans*, *Bacillus siamensis*, *Bacillus lautus*, *Bacillus clausii*, *Bacillus megaterium*, *Bacillus thuringiensis*, *Bacillus cereus*, *Bacillus firmus*, *Bacillus velezensis*, *Bacillus pichinotyi*, *Bacillus acidocaldarius*, *Bacillus alkalicola*, *Bacillus azotoformans*, *Bacillus anthracis*, *Bacillus badius*, *Bacillus bataviensis*, *Bacillus cycloheptanicus*, *Bacillus aneurinilyticus*, *Bacillus migulanus*, *Bacillus abyssalis*, *Bacillus aestuarii*, *Bacillus polymyxa*, and *Bacillus sp.*

Examples of bacteria of the genus *Paenibacillus* include *Paenibacillus macerans*, *Paenibacillus amylolyticus*, *Paenibacillus peoriate*, and *Paenibacillus elgii*.

Examples of bacteria of the genus *Geobacillus* include *Geobacillus thermoglucosidasius*, *Geobacillus caldoxylosilyticus*, and *Geobacillus stearothermophilus*.

Examples of bacteria of the genus *Clostridium* include *Clostridium butyricum*, *Clostridium kluyveri*, *Clostridium acetobutylicum*, *Clostridium aminobutyricum*, *Clostridium beijerinckii*, *Clostridium saccharoperbutylacetonicum*, *Clostridium thermocellum*, *Clostridium ljungdahlii*, and *Clostridium botulinum*.

Examples of bacteria of the genus *Sporosarcina* include *Sporosarcina pasteurii*, *Sporosarcina ureae*, *Sporosarcina psychrophila*, and *Sporosarcina thermotolerans*.

A bacterium to be cultured in the method of the present invention may be a non-genetic recombinant bacterium or a genetic recombinant bacterium, but preferably those containing no antibiotic resistance gene.

Further, a bacterium to be cultured in the method of the present invention may be a wild-type or variant strain, but even in the latter case, the bacterium preferably has no mutation in antibiotic resistance.

The method for producing bacterial cells and the method for culturing bacterium of the present invention comprise culturing a bacterium in a liquid medium containing an antibiotic.

The liquid medium can be appropriately selected depending on the kind of a bacterium to be cultured, and a general liquid medium containing medium components such as carbon sources and nitrogen sources at concentrations suitable for culturing bacteria can be used.

Examples of carbon sources include sugar (starch, glucose, lactose, glycerol, arabinose, ribose, xylose, galactose, fructose, mannose, inositol, mannitol, sorbitol, glucosamine, N-acetylglucosamine, cellobiose, maltose, sucrose, trehalose, xylitol, etc.) or sugar-source raw materials, alcohols, organic acids, organic acid salts, alkanes or other common carbon sources. Examples of nitrogen sources include soybean-derived components, yeast-derived components, corn-derived components, animal and plant proteins and the decomposition products thereof, ammonium salts such as ammonium nitrate, ammonium sulfate, ammonium chloride, and ammonium acetate, ammonia, sodium nitrate, potassium nitrate, sodium glutamate, and urea.

Examples of medium components other than carbon sources and nitrogen sources include trace metal salts, amino acids, and vitamins, which can be added as appropriate when necessary.

In the method of the present invention, the antibiotic is not particularly limited as long as it can reduce the appearance rate of abnormal colonies as compared with a case in which no antibiotic is added, and specific examples thereof include streptomycin, lincomycin, erythromycin, rifampicin, chloramphenicol, actinomycin, fusidic acid, lipiamycin, puromycin, spectinomycin, tetracycline, and thiostrepton. A particularly preferred example among these is streptomycin.

The antibiotic has preferably a concentration (less than a sublethal dose) that does not inhibit bacterial growth, and is preferably added so that the concentration of the antibiotic in a liquid medium is 0.001 ppm or more and 10,000 ppm or less.

The concentration of the antibiotic is preferably equal to or less than the growth inhibition concentration at which bacterial growth is inhibited. The concentration differs depends on the kind of bacteria, and is for example, preferably 1,000 ppm or less, more preferably 300 ppm or less, and further preferably 90 ppm or less. On the other hand, the lower limit of the concentration of the antibiotic may be any concentration that can suppress the appearance of abnormal colonies, and is preferably 0.01 ppm or more, more preferably 0.1 ppm or more, and further preferably 1 ppm or more.

The antibiotic is added to a liquid medium in a stage prior to the final stage. The antibiotic may be contained in the liquid medium at the start of culture or may be added during culture. When the antibiotic is added during culture, it is preferable to add when the cells have grown to a certain extent, for example, it is preferable to be added between 1 and 10 hours after the start of culture. Further, the concentration of the antibiotic in the liquid medium may be varied, for example, by supplementing with the antibiotic during culture.

The liquid culture step comprises two or more stages of culture with a subculture(s) of cells. The number of culture stages may be any number as long as it is two or more stages, but preferably it may be a multi-stage culture of two to four stages.

The number of culture vessels may be increased as the culture proceeds from first to later stages, such as one culture vessel is used in a first stage, four culture vessels are used in a second stage, and so on. Further, the capacity of the culture vessel may be increased as the culture proceeds from the first to the later stages, such as 1 L in the first stage, 10 L in the second stage, and so on.

Regarding the culture time of multi-stage culture, for example, an embodiment of a two-stage culture involves inoculating bacterial cells into a first-stage medium, culturing bacterial cells for 10 to 40 hours, and preferably 20 to 30 hours, inoculating a portion of the bacterial cells obtained by the first-stage culture into a second-stage medium, and then culturing bacterial cells for 15 to 80 hours, and preferably 20 to 50 hours. The total culture time ranges from preferably 25 to 120 hours, and more preferably 30 to 80 hours.

For example, an embodiment of a three-stage culture involves inoculating bacterial cells into a first-stage medium, culturing bacterial cells for 10 to 40 hours, and preferably 20 to 30 hours, inoculating a portion of the bacterial cells obtained by the first-stage culture into a second-stage medium, culturing bacterial cells for 5 to 40 hours, and preferably 10 to 30 hours, inoculating a portion of the bacterial cells obtained by the second-stage culture into a third-stage medium, and then culturing bacterial cells for 15 to 80 hours, and preferably for 20 to 50 hours. The total culture time ranges from preferably 30 to 160 hours, and more preferably 35 to 110 hours.

For example, an embodiment of a four-stage culture involves inoculating bacterial cells into a first-stage medium, culturing bacterial cells for 10 to 40 hours, and preferably 20 to 30 hours, inoculating a portion of the bacterial cells obtained by the first-stage culture into a second-stage medium, culturing bacterial cells for 5 to 40 hours, and preferably 10 to 30 hours, inoculating a portion of the bacterial cells obtained by the second-stage culture into a third-stage medium, culturing bacterial cells for 5 to 40 hours, and preferably for 10 to 30 hours, inoculating a portion of the bacterial cells obtained by the third-stage culture into a fourth-stage medium, and then culturing bacterial cells for 15 to 80 hours, and preferably for 20 to 50 hours. The total culture time ranges from preferably 35 to 200 hours, and more preferably 60 to 140 hours.

As described above, when liquid culture is performed in multiple stages, culture is performed using a medium containing an antibiotic in at least one of the stages except for the final stage, and in the final stage, culture is performed with an antibiotic the concentration of which is lower than that in the stage where the antibiotic is contained. Lowering the concentration of the antibiotic in the final stage results in exclusion of factors causing growth inhibition and sporulation inhibition, so that the culture step can proceed more rapidly. In general, when microorganisms are produced by multi-stage culture, the final stage may be the largest in scale. Hence, lowering the concentration of an antibiotic in the final stage leads to suppression of the production cost.

For example, the concentration of an antibiotic in the final stage may be ½ or less, ⅕ or less, ¹⁄₁₀ or less, ¹⁄₅₀ or less, or ¹⁄₁₀₀ or less of the concentration of the antibiotic in a prior stage in which the antibiotic is contained. The concentration of an antibiotic in the final stage may also be zero (below the detection limit).

For example, as in Example 1 described later, a culture method may also be employed, which involves culturing in three stages including the first and second stages with antibiotic addition and the third stage with no antibiotic addition, and transferring 1% of the culture solution of the second stage to the third stage, so as to lower the concentration of the antibiotic to a level ¹⁄₁₀₀ of that in the second stage.

Further, the concentration of an antibiotic can be gradually reduced stage by stage as the stages proceed. In this case, the concentration of the antibiotic in the final stage can be ½ or less, ⅕ or less, ¹⁄₁₀ or less, ¹⁄₅₀ or less, or ¹⁄₁₀₀ or less of the maximum concentration.

The period for culturing with a medium containing an antibiotic is preferably 10 hours or more in total.

The culture temperature can be appropriately selected depending on the kind of bacteria, and ranges from, for example, 10° C. to 50° C., preferably 15° C. to 50° C., and more preferably 15° C. to 40° C.

Other various conditions such as oxygen concentration and pH may be conditions that are employed for general liquid culture of bacteria, such as conditions where bacteria are cultured while stirring under aerobic conditions (for example, oxygen concentration of 15% to 50%). The pH of the medium ranges from preferably 6.5 to 8.5, and more preferably 7.0 to 8.0.

Whether or not abnormal colonies appear can be confirmed by collecting a portion of cells obtained after liquid culture using an antibiotic(s), diluting the portion to a concentration that prevents the colonies from adhering to each other and enables the identification of the colony morphology, applying the resultant onto a solid medium such as agar medium for culturing, and then observing the morphology of the appearing colonies.

The term "abnormal colonies" refers to colonies exhibiting morphology different from that of wild-type bacterial colonies. For example, as shown in Table 3, normal colonies are approximately circular in shape, sides are in the form of lens, and the surface is smooth or mucoid, while abnormal colonies are irregular in shape and have flat sides and rough surface. When a colony has at least one of abnormal morphology, abnormal sides, and abnormal surface, it can be determined as an abnormal colony. The drawing depicts an example of the morphology of abnormal colonies, and the circled colonies are abnormal colonies.

EXAMPLES

The present invention will be described specifically with reference to Examples below, but the present invention is not limited to these Examples.

Example 1

Using a 500 mL Erlenmeyer flask (with a baffle), 100 mL each of liquid medium containing the components of the medium listed in Table 1 was prepared, and then autoclave sterilization was performed. In order to avoid the Maillard reaction, glucose was separately sterilized and mixed aseptically.

TABLE 1

Medium Composition

| Component | Manufacturer | Concentration (g/L) |
| --- | --- | --- |
| Glucose | Wako Pure Chemical Industries Ltd. | 25.0 |
| Defatted soy flour | Ajinomoto Healthy Supply Co., Inc. | 20.0 |
| Corn steep liquor | Difco | 5.0 |
| Yeast extract | Roquette | 4.0 |
| $MnCl_2 \cdot 4H_2O$ | Difco | 0.18 |
| NaCl | Wako Pure Chemical Industries Ltd. | 1.00 |
| $KH_2PO_4$ | Wako Pure Chemical Industries Ltd. | 0.50 |
| $MgSO_4 \cdot 7H_2O$ | Wako Pure Chemical Industries Ltd. | 0.63 |
| $CaCl_2$ | Wako Pure Chemical Industries Ltd. | 0.19 |
| $FeSO_4$ | Wako Pure Chemical Industries Ltd. | 0.00038 |

The test sections were set as described in Table 2. According to the conditions for each test section, an aqueous solution of filter-sterilized streptomycin was aseptically added to the medium.

One platinum loop was taken from a colony of *Bacillus subtilis* ITB 105 strain (NITE BP-01727) grown on a common agar medium and inoculated, and then shake culture was performed at 30° C. and 150 rpm (first stage). Eighteen hours later, 1 mL of each culture solution was aliquoted and transferred to a fresh medium, and then shaking culture was performed in the same manner (second stage). After 24 hours, 1 mL of each culture solution was aliquoted and then transferred to a fresh medium, and then shaking culture was performed in the same manner (third stage). The third-stage culture solution was sampled after 30 hours.

TABLE 2

Test Section Setting

| Test section No. | First-stage culture | | Second-stage culture | | Third-stage culture | |
| --- | --- | --- | --- | --- | --- | --- |
| | Type of antibiotic added | Concentration for addition (ppm) | Type of antibiotic added | Concentration for addition (ppm) | Type of antibiotic added | Concentration for addition |
| 1 | — | — | — | — | — | — |
| 2 | Streptomycin | 5 | Streptomycin | 5 | — | — |
| 3 | Streptomycin | 10 | Streptomycin | 10 | — | — |
| 4 | Streptomycin | 15 | Streptomycin | 15 | — | — |
| 5 | Streptomycin | 20 | Streptomycin | 20 | — | — |
| 6 | Streptomycin | 30 | Streptomycin | 30 | — | — |
| 7 | Streptomycin | 30 | Streptomycin | 30 | Streptomycin | 30 |

The resulting culture solutions were each diluted $1 \times 10^7$ folds with sterile water, and 100 µL of the diluted solution was applied to a common agar medium and then cells were cultured overnight at 37° C. The number of colonies that had appeared was determined to calculate CFU. Colonies that had appeared and clearly differed in colony morphology compared with the parent strain on the basis of the criteria in Table 3 were determined as abnormal colonies and the number of the abnormal appearing colonies was determined and then the proportion thereof in the total number of colonies was calculated. The results are shown in Table 4. As a result, in the three-stage culture, abnormal appearing colonies accounted for about 5% when no antibiotic was added. However, when cells were cultured by adding streptomycin in the first and second stages, and none in the third stage, no appearance of abnormal colonies was observed. Further, when streptomycin was added in all of the first, second and third stages, although no abnormal colony appeared, the number of appearing colonies and the number of normal appearing colonies were low, and the productivity of bacterial cells was lower than those of Test section Nos. 2 to 6.

TABLE 3

Determination Criteria for Colony Morphology

| Item | Wild-type (Initial stage of culture) | Wild-type (late stage of culture) | Abnormal |
| --- | --- | --- | --- |
| Shape | Circular | Circular | Circular or irregular |
| Side | Lens-shaped | Crater-shaped or Angular | Flat |
| Surface | Mucoid or smooth | Smooth or wrinkled | Rough |

TABLE 4

Test Results

| Test section No. | Culture stage | Culture time (hour) | CFU (/mL) | Number of normal colonies | Number of abnormal colonies | Appearance (%) of abnormal colonies |
| --- | --- | --- | --- | --- | --- | --- |
| 1 | Third stage | 30 | 9.9e+09 | 94 | 5 | 5.1% |
| 2 | Third stage | 30 | 8.8e+09 | 88 | 0 | 0.0% |
| 3 | Third stage | 30 | 1.09e+10 | 109 | 0 | 0.0% |
| 4 | Third stage | 30 | 7.0e+09 | 70 | 0 | 0.0% |
| 5 | Third stage | 30 | 8.2e+09 | 82 | 0 | 0.0% |
| 6 | Third stage | 30 | 6.3e+09 | 63 | 0 | 0.0% |
| 7 | Third stage | 30 | 4.9e+09 | 49 | 0 | 0.0% |

What is claimed is:

1. A method for producing *Bacillus subtilis* bacterial cells, comprising, in a multi-stage liquid culture process:
    culturing a *Bacillus subtilis* bacterium in a liquid medium comprising an antibiotic in a stage prior to the final stage; and then
    lowering the concentration of the antibiotic in the final stage to a level lower than that in the prior stage,
    wherein the antibiotic is at least one selected from the group consisting of streptomycin, lincomycin, and chloramphenicol,
    wherein the concentration of the antibiotic in the liquid medium in the stage prior to the final stage ranges from 1.0 ppm to 90 ppm, and
    wherein the concentration of the antibiotic in the final stage is $1/10$ or less of the maximum concentration of the antibiotic in the liquid medium.

2. A method for culturing a *Bacillus subtilis* bacterium exhibiting reduced appearance of variants forming an abnormal colony, the method comprising, in a multi-stage liquid culture process:
    culturing a *Bacillus subtilis* bacterium in a liquid medium comprising an antibiotic in a stage prior to the final stage; and then
    lowering the concentration of the antibiotic in the final stage to a level lower than that in the prior stage,
    wherein the antibiotic is at least one selected from the group consisting of streptomycin, lincomycin, and chloramphenicol,
    wherein the concentration of the antibiotic in the liquid medium in the stage prior to the final stage ranges from 1.0 ppm to 90 ppm, and
    wherein the concentration of the antibiotic in the final stage is $1/10$ or less of the maximum concentration of the antibiotic in the liquid medium.

3. A method for suppressing an appearance and a growth of variants forming an abnormal colony during liquid culture of *Bacillus subtilis* bacteria, the method comprising, in a multi-stage liquid culture process:
    culturing a *Bacillus subtilis* bacterium in a liquid medium comprising an antibiotic in a stage prior to the final stage; and then
    lowering the concentration of the antibiotic in the final stage to a level lower than that in the prior stage,
    wherein the antibiotic is at least one selected from the group consisting of streptomycin, lincomycin, and chloramphenicol,
    wherein the concentration of the antibiotic in the liquid medium in the stage prior to the final stage ranges from 1.0 ppm to 90 ppm, and
    wherein the concentration of the antibiotic in the final stage is $1/10$ or less of the maximum concentration of the antibiotic in the liquid medium.

* * * * *